United States Patent [19]

Wilkinson et al.

[11] 4,403,604
[45] Sep. 13, 1983

[54] GASTRIC POUCH

[76] Inventors: Lawrence H. Wilkinson; Lanette L. Wilkinson, both of 1516 Columbia Dr., NE., Albuquerque, N. Mex. 87106

[21] Appl. No.: 378,004

[22] Filed: May 13, 1982

[51] Int. Cl.³ .............................................. A61B 19/00
[52] U.S. Cl. ........................................... 128/1 R; 3/1
[58] Field of Search .............. 128/1 R, 132 R, 132 D, 128/133; 2/1; 3/1

[56] References Cited

U.S. PATENT DOCUMENTS

| | | | |
|---|---|---|---|
| 3,875,928 | 4/1975 | Angelchik | 128/1 R |
| 3,983,863 | 10/1976 | Tanke et al. | 128/1 R |
| 4,217,890 | 8/1980 | Owens | 128/1 R |

Primary Examiner—Stephen C. Pellegrino
Attorney, Agent, or Firm—Harvey B. Jacobson

[57] ABSTRACT

A generally rectangular flexible wrap panel having longitudinally spaced inwardly tapering and outwardly opening opposite side marginal notches formed therein intermediate its opposite ends is provided and the outer margin of a radially split annular flexible yoke panel is secured across one end of the wrap panel. Opposing edges of the wrap panel defining the notches are then overlapped and secured together to form darts in the wrap panel and the wrap panel is placed along the greater curvature of the stomach with the collar panel registered with the esophagogastric junction. The side marginal edges of the wrap panel are then wrapped about the stomach toward the lesser curvature, overlapped and sutured together and the circumferential ends of the yoke panel are overlapped and sutured together about the esophagogastric junction and the end edges of the collar panel are sutured together about the esophagus.

7 Claims, 5 Drawing Figures

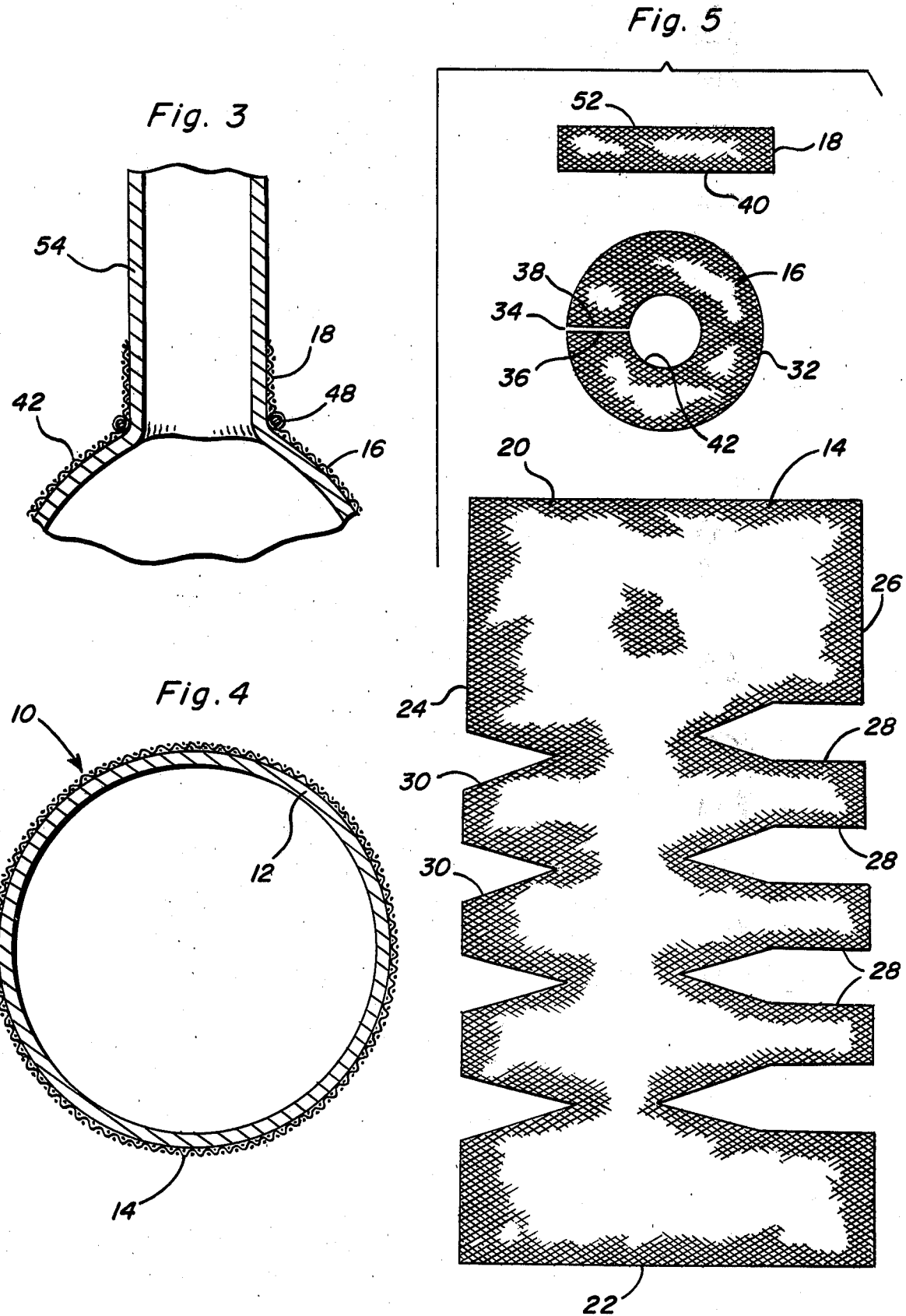

GASTRIC POUCH

BACKGROUND OF THE INVENTION

In recent years there have been several different surgical procedures which have been attempted to correct morbid obesity. These various attempts have included gastric bypasses, small-bowel bypasses and other radical procedures. While these procedures have proven more effective than psychiatric or dietary regimens in achieving substantial and lasting reduction for morbidly obese patients, they have often resulted in frequent and serious physiologic and metabolic derangements. For these reasons, at least one study was begun to develop a more physiologic operation that would reduce caloric intake without altering the continuity of the gastro intestinal track. The objective at the outset of this study was to reduce the reservoir capacity of the stomach and thereby achieve early satiety.

As a result of the aforementioned study, experiments were made on animals involving the inversion of the greater curvature of the stomach. Postoperatively, these animals could eat only small amounts without vomiting and all lost weight. However, within a relatively short period of time following surgery they were observed to be eating progressively larger meals and soon regained normal weight. By tests then made on the animals, it was revealed that their stomachs had regained their normal size and shape. Accordingly, a more lasting method of reducing the reservoir capacity of the stomach was needed. Such a more lasting method comprises the subject of the instant invention wherein the stomach is wrapped in a mesh panel which may be constructed of various materials to be hereinafter more fully set forth. Such a mesh panel does not allow the stomach to expand beyond a predetermined size and may be removed by a subsequent operation, if and when such removal is deemed prudent.

Although various wraps and flexible supportive panels heretofore have been provided such as those disclosed in U.S. Pat. Nos. 3,111,943, 3,863,639, 3,983,863 and 4,217,890, these wraps and supportive panels are not readily adaptable as wraps for the stomach or usable for the purpose of a stomach wrap.

BRIEF DESCRIPTION OF THE INVENTION

The gastric pouch of the instant invention is constructed of three panels including a main panel, a yoke panel and a collar panel secured together along adjacent marginal edges and the wrap panel has darts formed in its opposite side longitudinal edge portions in order to conform the wrap panel to the shape of the stomach. The yoke panel is specifically designed to conform to esophagogastric junction and the collar panel is of a size and shape adapted for securement of the resultant wrap about the lower end of the esophagus.

The main object of this invention is to provide a gastric pouch or wrap of a construction which will facilitate its manufacture from sheet panels of suitable flexible materials such as a mesh material and which may be secured about the stomach in order to prevent expansion of the stomach beyond a predetermined size. In this manner, the reserve capacity of the stomach is substantially reduced and early satiety results together with a substantial reduction of weight, in most cases.

Another object of this invention is to provide a stomach pouch or wrap which may be surgically applied for the intended purpose and by a procedure which is relatively free of postoperative complications.

Still another important object of this invention is to provide a gastric pouch or wrap in accordance with the preceding objects and constructed and applied in a manner such that subsequent removal of the pouch or wrap may be effected with minimum chance of postoperative complications.

A final object of this invention to be specifically enumerated herein is to provide a gastric pouch or wrap in accordance with the preceding objects and which may be inexpensively produced, utilized to perform the intended procedure with a minimum of risk and which will be effective in achieving substantial reduction of morbid obesity, in most cases.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is an enlarged fragmentary sectional view taken substantially upon the plane indicated by the section line 3—3 of FIG. 1;

FIG. 4 is an enlarged sectional view taken substantially upon the plane indicated by the section line 4—4 of FIG. 1; and FIG. 5 is an exploded plan view of the three basic panels which may be sewn together and about the stomach to form the gastric pouch of the instant invention.

DETAILED DESCRIPTION OF THE INVENTION

Figure 1:
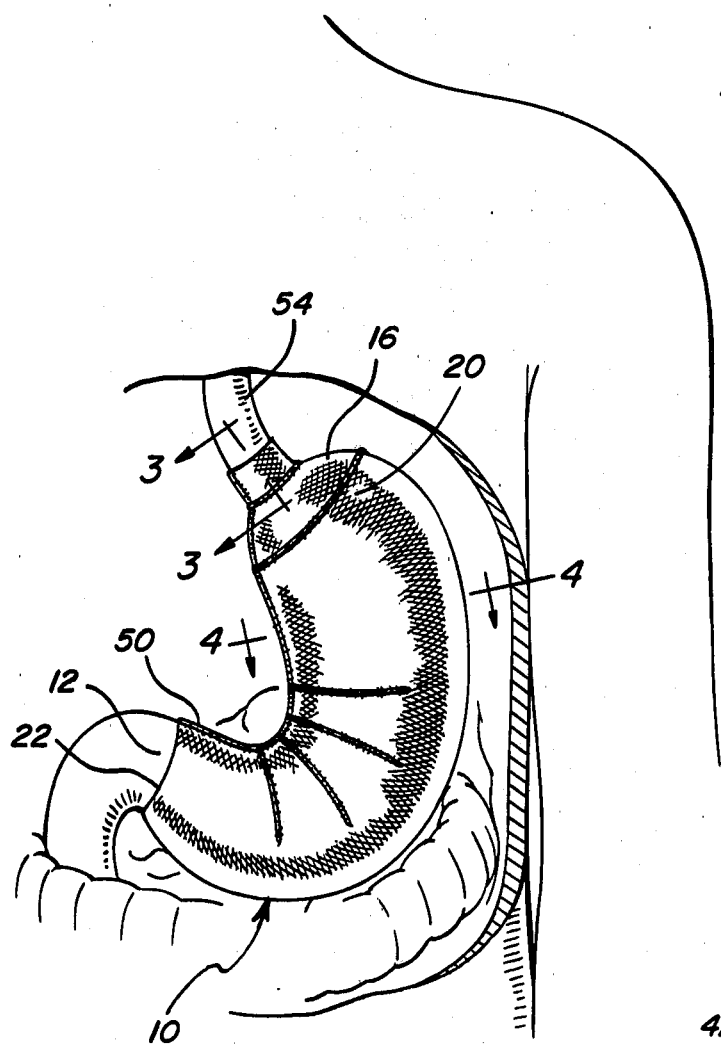
FIG. 1 is a perspective view illustrating the gastric pouch as applied to the stomach of a patient.
Figure 2:
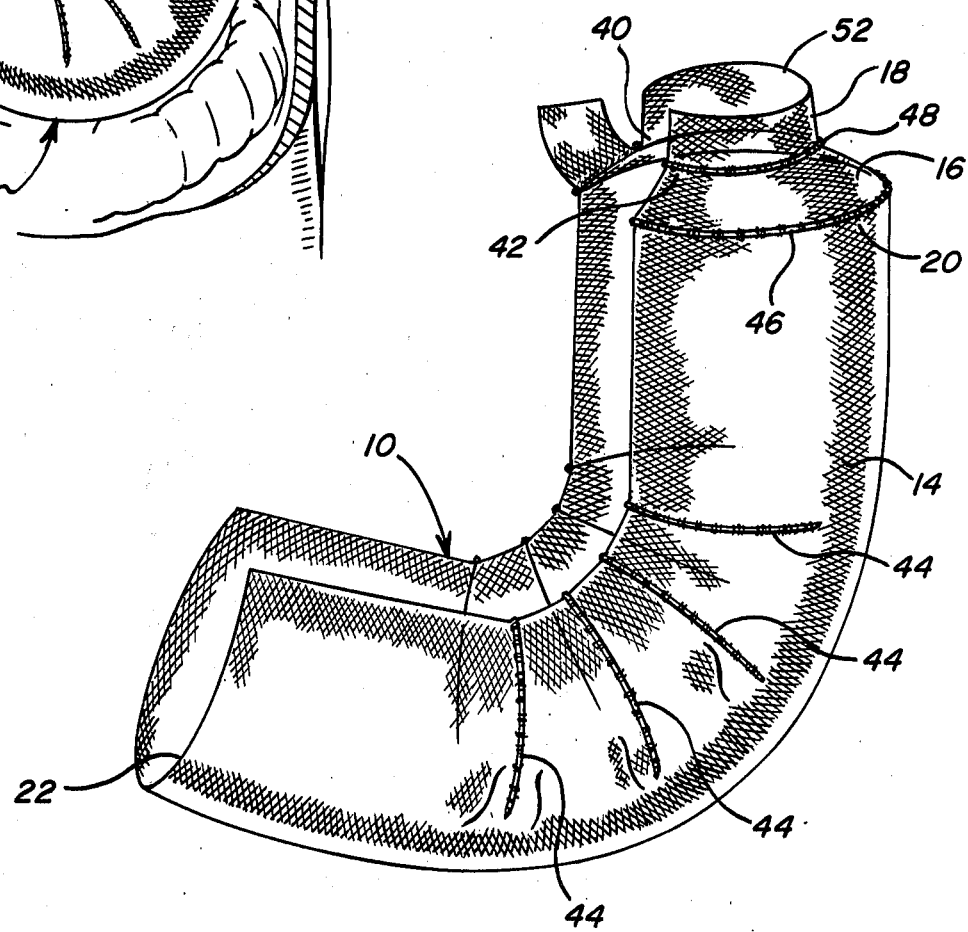
FIG. 2 is an enlarged perspective view of the pouch or wrap immediately prior to application to the stomach.

Referring now more specifically to the drawings, the numeral 10 generally designates the gastric pouch of the instant invention and the pouch 10 is illustrated in FIG. 2 in its configuration immediately prior to application to a stomach and in FIG. 1 as fully applied to a stomach 12.

The pouch 10 is constructed of three panels 14, 16 and 18. The plan shapes of the panels 14, 16 and 18 are clearly shown in FIG. 5. With attention first to the panel 14 which may be termed a wrap panel, the panel 14 may be seen to be substantially rectangular in plan shape including opposite ends 20 and 22 and opposite side marginal edge portions 24 and 26. The side marginal edge portion 26 includes laterally outwardly opening and inwardly tapering notches 28 formed therein at points spaced longitudinally therealong intermediate the opposite ends of the panel 14 and the side marginal edge 24 has slightly smaller laterally outwardly opening and inwardly tapering notches 30 formed therein at points spaced therealong intermediate the opposite ends 20 and 22 of the panel 14. The notches 30 are slightly out of transverse registry with the notches 28 and in forming the pouch or wrap 10, the outer circumstance 32 of the annular yoke panel 16 is sutured along the end 20 of the panel 14. The annular panel 16 includes a radial slot 34 which defines closely opposing circumferential end edges 36 and 38 of the panel 32 and the panel 16 is secured to the panel 14 in a manner such that the end edges 36 and 38 are substantially coextensive with the opposite side longitudinal edges 24 and 26 of the panel 14.

After the yoke panel 16 has been secured to the panel 14, one longitudinal edge 40 of the elongated strip panel 18 is sutured to the inner circumstance 42 of the panel 16. Thereafter, the opposing edges of the panel 14 defining the notches 28 and 30 are lapped over each other and sutured together as at 44 in order to conform the wrap or pouch 10 to the general shape of the stomach 12. The suturing used to secure the panel 16 to the panel 14 is illustrated as at 46 and the suturing utilized to secure the panel 18 to the panel 16 is illustrated as at 48.

After the wrap or pouch 10 has been sutured together to the extent illustrated in FIG. 2, the wrap or pouch 10 may be applied along the greater curvature of the stomach 12 and the side marginal edges 24 and 26 of the panel 14 may be deflected over the lesser curvature of the stomach 12 toward each other and overlapped and sutured together as at 50. The suturing at 50 is carried out in order to secure the wrap 10 snugly about the stomach 12. Thereafter, the ends of the panels 16 and 18 are sutured together to secure those panels about esophagogastric junction and the lower end of the esophagus, respectively.

It is to be noted that the current technique in applying the pouch 10 to a stomach 12 involves preoperatively and every six hours postoperatively for 48 hours, 2 g of cephalosporin is given intravenously. Following induction of an anesthesia, the patient is placed in 20° Trendelenburg's position for 30 seconds. This is repeated every 30 minutes during the procedure, and in the recovery room to empty leg veins, hoping thereby to reduce the instance of thrombophlebitis.

The abdomen is entered through a midline incision from the xyphoid to umbilicus. The abdomen is carefully explored. The gastrocolic omentum is divided, leaving the right-sided gastroepiploic vessels attached to the stomach; as little fat as possible is left on the stomach.

At this point, a self-retaining retractor is inserted and the operating table is placed in reverse Trendelenburg's position with the head elevated 20° so that the intestines will fall away from the diaphragm. These two maneuvers greatly aid exposure.

The anesthetist then inserts a gastric tube transorally into the stomach and it is positioned with its tip 4 to 5 cm beyond the esophagogastric junction. The short gastric vessels are divided between metal clips are hemostasis. Metal clips on the gastric side are replaced with ligatures, since enclosing these inside the wrap may lead to gastric perforation. The gastrohepatic omentum is divided, and the esophagus with the right vagus nerve is carefully mobilized.

The fat pad at His's angle is excised. Inversion of the lesser curvature of the stomach is begun by performing a "floppy" Nissen's fundoplication. It is important to mark the exact points on the front and back of the fundus that should be approximated when the fundus is brought around the esophagus. Two to four interrupted sutures of 000 polypropylene on intestinal needles are used to form the Nissen's fundoplication, which extends down to the left gastric artery. Experience has shown it is not necessary to invert the lesser curvature below the level of the left gastric artery before snugly applying the wrap.

The wrap or pouch 10, as illustrated in FIG. 2, is now placed about stomach 12 in the manner previously described. The various panels 14, 16 and 18 may be constructed of either TEFLON, DACRON or polypropylene. Further, it is also deemed that DACRON impregnated with silicone may be used in an attempt to reduce undesirable reactions to the operation and also to make removal of the wrap or pouch 10, if such removal is necessary, quite easy.

The use of the yoke panel 16 at the esophagogastric junction is very important in that it insures a wrap or pouch which closely conforms to the corresponding area of the stomach and enables a more complete wrap of the stomach and lower esophagus. When the darts are formed by the stitching 44, frequent chain stitch knots are used to avoid wrinkling. The short darts are disposed along the lesser curvature of the interior layer of the wrap. The midline of the panel 14 substantially midway between the apices of the notches 28 and 30 rests along the greater curvature of the stomach and the excess of the posterior end of the wrap 10 is excised if unneeded.

The wrap is sutured loosely around the esophagus and inverted upper stomach. From the level of the left-sided gastric artery to the prepyloric region, the stomach is wrapped snugly without a bougie in the lumen. A variable amount of fat about Laterjet's nerves and the gastric vessels is unavoidably included inside the wrap, but this fat will atrophy in a short time. The gastrocolic omentum is then placed between the wrapped stomach and the left lobe of the liver.

Actual procedures as above described have been achieved with considerable success and with minimum postoperative complications.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. The method of reduction of the capacity of a stomach, said method comprising the provision of an elongated generally rectangular flexible wrap panel having opposite ends and opposite side marginal edges and with the opposite side marginal edges each including longitudinally spaced laterally outwardly opening and inwardly tapering notches formed therein intermediate the opposite ends of the panel, a generally annular flexible yoke panel having adjacent opposing ends and a narrow elongated flexible strip panel, suturing the outer periphery of the yoke panel across one end of the wrap panel, suturing one longitudinal edge of the strip panel to the inner peripheral edge of the yoke panel, overlapping and suturing together the opposing edges of the wrap panel defining each notch to form darts in the panel and thereby conform the wrap panel to the shape of a stomach, placing the wrap panel along the greater curvature of the stomach with the central longitudinal zone of the wrap panel inwardly of the notches generally centered relative to the greater curvature, and thereafter suturing the opposite side marginal edges of the wrap panel snugly about the stomach, suturing the opposing ends of the yoke panel together about the esophagogastric junction and suturing the opposite ends of the strip panel together about the esophagus as well.

2. The method of claim 1 wherein said panels comprise mesh panels.

3. The method of claim 2 wherein said panels are constructed of inert fabric material.

4. A gastric pouch comprising an elongated panel of mesh material having opposite longitudinal edges laterally outwardly opening and inwardly tapering notches formed therein at points spaced longitudinally therealong intermediate the opposite ends of said elongated panel, an annular yoke panel including a radial slot formed therethrough defining closely opposing arc end edges of said yoke panel, the outer circumferential edge of said yoke panel being sutured across one end of said wrap panel, an elongated strip panel having a first longitudinal edge thereof sutured to the inner circumferential edge of said yoke panel, and the opposing edges of said panel defining each of said notches being sutured together to form darts in said wrap panel and thereby contour said wrap panel for disposition about said stomach with the approximate longitudinal midline of the wrap panel extending along the greater stomach curvature.

5. The pouch of claim 4 wherein said panels are constructed of mesh material.

6. The pouch of claim 5 wherein said mesh material is constructed of an inert plastic material.

7. The pouch of claim 4 wherein the lateral inward extent of the notches formed in one of said longitudinal edges is greater than the lateral inward extent of said notches formed in the other of said longitudinal edges.

* * * * *